US012653414B2

(12) United States Patent
Yoon et al.

(10) Patent No.: US 12,653,414 B2
(45) Date of Patent: Jun. 16, 2026

(54) MAGNETIC PARTICLE IMAGING DEVICE APPLICABLE TO HUMAN

(71) Applicant: GIST(Gwangju Institute of Science and Technology), Gwangju (KR)

(72) Inventors: Jung Won Yoon, Gwangju (KR); Tuan Anh Le, Gwangju (KR); Minh Phu Bui, Gwangju (KR)

(73) Assignee: GIST(Gwangju Institute of Science and Technology), Gwangju (KR)

( * ) Notice: Subject to any disclaimer, the term of this patent is extended or adjusted under 35 U.S.C. 154(b) by 13 days.

(21) Appl. No.: 18/366,897

(22) Filed: Aug. 8, 2023

(65) Prior Publication Data

US 2024/0215847 A1 Jul. 4, 2024

(30) Foreign Application Priority Data

Dec. 29, 2022 (KR) ........................ 10-2022-0189666

(51) Int. Cl.
    *A61B 5/0515* (2021.01)
    *G01R 33/00* (2006.01)
    *G01R 33/12* (2006.01)

(52) U.S. Cl.
    CPC ........ *A61B 5/0515* (2013.01); *G01R 33/0005* (2013.01); *G01R 33/1276* (2013.01)

(58) Field of Classification Search
    CPC .............. A61B 5/0515; G01R 33/0005; G01R 33/1276; G01R 33/0023; G01R 33/34
    See application file for complete search history.

(56) References Cited

U.S. PATENT DOCUMENTS

| | | | | |
|---|---|---|---|---|
| 2011/0089942 A1* | 4/2011 | Goodwill | ........... | G01R 33/1276 |
| | | | | 600/407 |
| 2011/0221438 A1* | 9/2011 | Goodwill | ............. | A61B 5/0515 |
| | | | | 324/301 |

(Continued)

FOREIGN PATENT DOCUMENTS

| | | | | |
|---|---|---|---|---|
| WO | WO-2011121487 A1 * | 10/2011 | ........... | A61B 5/0515 |
| WO | WO-2022092402 A1 * | 5/2022 | ......... | G01R 33/0005 |

OTHER PUBLICATIONS

Le, Tuan-Anh, Minh Phu Bui, and Jungwon Yoon. "Design of a rabbit scale 3D magnetic particle imaging system with amplitude modulation." International Journal on Magnetic Particle Imaging IJMPI 6.2 Suppl 1 (2020) (Year: 2020).*

(Continued)

*Primary Examiner* — Sean D Mattson
(74) *Attorney, Agent, or Firm* — Studebaker Brackett PLLC

(57) ABSTRACT

The present disclosure relates to a magnetic particle imaging device having a field of view (FOV) wide enough to be applicable to the human body. A magnetic particle imaging device according to some embodiments includes at least: an FFP generation unit generating a field free point (FFP) in a FOV; first to third operation coil units moving the FFP in first to third directions which are vertical to each other, respectively; an excitation coil unit generating a magnetic field in the FOV, and exciting a magnetic particle in the FOV; a reception coil unit receiving a magnetic signal generated from the magnetic particle; and a processor dividing the FOV into a plurality of partial FOVs, controlling the first to third operation coil units so that the FFP moves in each partial FOV, and generating an image for the FOV based on the magnetic signal for each partial FOV.

7 Claims, 14 Drawing Sheets

(56)                    References Cited

U.S. PATENT DOCUMENTS

2012/0153948 A1 *   6/2012   Rahmer .................. A61B 5/05
                                              324/301
2018/0335487 A1 *   11/2018   Tonyushkin ....... G01R 33/1276

OTHER PUBLICATIONS

Zhang, Xingming, et al. "A soft magnetic core can enhance navigation performance of magnetic nanoparticles in targeted drug delivery." IEEE/ASME Transactions on Mechatronics 23.4 (2018): 1573-1584. (Year: 2018).*

* cited by examiner pFOV1    pFOV2

FFP    FFP

FOV

MAGNETIC PARTICLE IMAGING DEVICE APPLICABLE TO HUMAN

CROSS-REFERENCE TO RELATED APPLICATIONS

This application claims the priority of Korean Patent Application No. 10-2022-0189666 filed on Dec. 29, 2022, in the Korean Intellectual Property Office, the disclosure of which is incorporated herein by reference.

BACKGROUND OF THE INVENTION

Field of the Invention

The present invention relates to a magnetic particle imaging device having a field of view (FOV) wide enough to be applicable to the human body.

Description of the Related Art

Compared to Magnetic Resonance Imaging (MRI) devices or X-ray devices, Magnetic Particle Imaging (MPI) devices have a limitation in that the MPI devices cannot acquire anatomical images, but have an advantage in that the MPI devices can specify and image lesion portions such as cancer, so recent development is being actively conducted as a next-generation medical device that can replace Positron Emission Tomography (PET).

The magnetic particle imaging device overlaps two or more magnetic fields to generate a field free point (hereinafter, referred to as FFP) where the magnetic field is sparse, excites a magnetic particle which is present within the point, and then generates an image based on a signal generated from a particle.

The conventional magnetic particle imaging device has been used limitedly for acquiring a high-resolution image of a small animal due to magnetic field restrictions for preventing a peripheral nerve stimulation (PNS).

In order to apply the magnetic particle imaging device to the human body, it is necessary to secure a wide field of view (FOV), and to this end, when a size of a core is increased, a magnetic gradient field ([T/m]) in the FOV rapidly decreases, so the resolution of the image is lowered.

Accordingly, in order to apply the magnetic particle imaging device to a clinical demonstration, a magnet particle imaging device capable of a high-resolution image while securing the wide FOV is required.

SUMMARY OF THE INVENTION

The present invention has been made in an effort to provide a magnetic particle imaging device capable of acquiring a high-resolution image for a wide FOV.

The objects of the present invention are not limited to the above-mentioned objects, and other objects and advantages of the present invention that are not mentioned can be understood by the following description, and will be more clearly understood by embodiments of the present invention. Further, it will be readily appreciated that the objects and advantages of the present invention can be realized by means and combinations shown in the claims.

In order to achieve the object, a magnetic particle imaging device according to an exemplary embodiment of the present invention includes: an FFP generation unit generating a field free point (FFP) in a field of view (FOV); first to third operation coil units moving the FFP in first to third directions which are vertical to each other, respectively; an excitation coil unit generating a magnetic field in the FOV, and exciting a magnetic particle in the FOV; a reception coil unit receiving a magnetic signal generated from the magnetic particle; and a processor dividing the FOV into a plurality of partial FOVs, controlling the first to third operation coil units so that the FFP moves in each partial FOV, and generating an image for the FOV based on the magnetic signal for each partial FOV.

In an exemplary embodiment, the FFP generation unit includes a pair of selection coils disposed to be opposite to each other in the first direction with the FOV interposed therebetween.

In an exemplary embodiment, the magnetic particle imaging device further includes a pair of core surrounded by the one pair of selection coils.

In an exemplary embodiment, the FFP generation unit includes a pair of superconductors disposed to be opposite to each other in the first direction with the FOV interposed therebetween.

In an exemplary embodiment, the first operation coil unit includes a pair of first focus coils and a pair of first drive coils that are disposed to be opposite to each other in the first direction, and generate the magnetic field in the first direction, and move the FFP in the first direction.

In an exemplary embodiment, the second operation coil unit includes a pair of second focus coils and a pair of second drive coils that are disposed to be opposite to each other in the second direction, and generate the magnetic field in the second direction, and move the FFP in the second direction.

In an exemplary embodiment, the third operation coil unit includes a pair of third drive coil that is disposed to be extended in the third direction, and generate the magnetic field in the third direction, and move the FFP in the third direction.

In an exemplary embodiment, the excitation coil unit excites the magnetic particle by mixing a harmonic magnetic field with the magnetic fields generated in the first to third operation coil units.

In an exemplary embodiment, the reception coil unit is disposed to be surrounded by an inner circumference surface of the excitation coil unit, and includes a first reception coil wound in one direction and a second reception coil disposed to be spaced in a third direction and wound in the other direction which is an opposite direction to one direction.

In an exemplary embodiment, the processor primarily controls the first to third operation coil units so that the FFP moves into the partial FOV, and secondarily controls the first to third operation coil units so that the FFP moves into the partial FOV.

In an exemplary embodiment, the processor controls the first and second focus coils so that the FFP moves into the partial FOV, and controls the first to third drive coils so that the FFP moves within the partial FOV.

In an exemplary embodiment, amplitudes of the magnetic field generated in the first and second focus coils are larger than amplitudes of the magnetic fields generated in the first to third drive coils, and frequencies of the magnetic field generated in the first and second focus coils are lower than frequencies of the magnetic fields generated in the first to third drive coils.

In an exemplary embodiment, the processor includes a processor that generates a partial image for the each partial FOV based on the magnetic signal for each partial FOV, and generates the entire image for the FOV by combining the partial image.

According to the present invention, there is an advantage in that the FOV is divided into multiple partial FOVs and image for respective partial FOVs are acquired and combined to acquire an image for an entire FOV, thereby acquiring a high-definition for the FOV, and applying the present invention to a clinical demonstration without a peripheral nerve stimulation. In addition to the above-described effects, the specific effects of the present invention are described together while describing specific matters for implementing the invention below.

DETAILED DESCRIPTION OF THE PREFERRED EMBODIMENT

Figure 1:
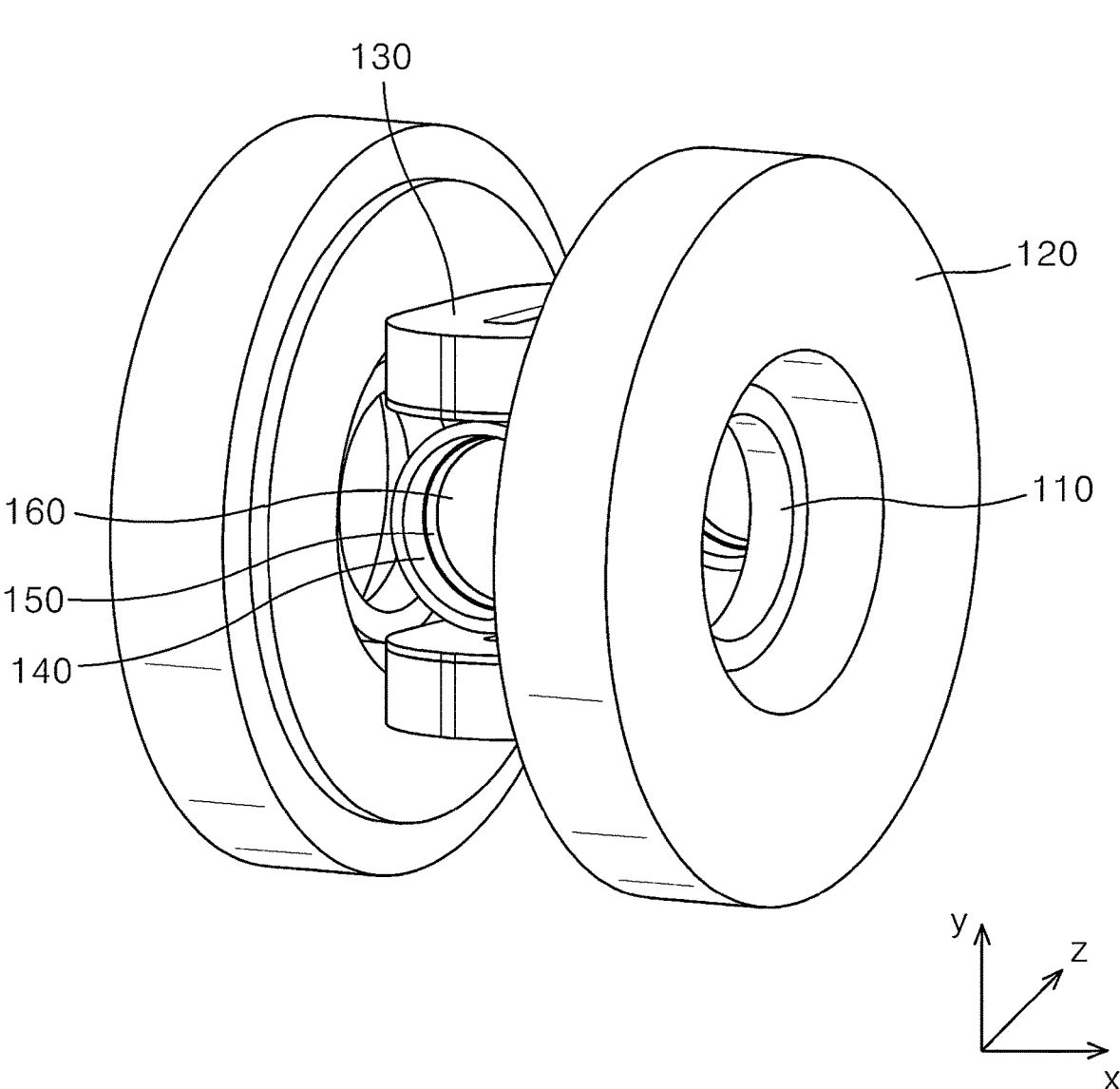
FIGS. 1 and 2 are diagrams illustrating a magnetic particle imaging device according to each embodiment of the present invention.

The above-mentioned objects, features, and advantages will be described in detail with reference to the drawings, and as a result, those skilled in the art to which the present invention pertains may easily practice a technical idea of the present invention. In describing the present invention, a detailed description of related known technologies will be omitted if it is determined that they unnecessarily make the gist of the present invention unclear. Hereinafter, a preferable embodiment of the present invention will be described in detail with reference to the accompanying drawings. In the drawings, the same reference numeral is used for representing the same or similar components.

Although the terms "first", "second", and the like are used for describing various components in this specification, these components are not confined by these terms. The terms are used for distinguishing only one component from another component, and unless there is a particularly opposite statement, a first component may be a second component, of course.

Further, in this specification, any component is placed on the "top (or bottom)" of the component or the "top (or bottom)" of the component may mean that not only that any configuration is placed in contact with the top surface (or bottom) of the component, but also that another component may be interposed between the component and any component disposed on (or under) the component.

In addition, when it is disclosed that any component is "connected", "coupled", or "linked" to other components in this specification, it should be understood that the components may be directly connected or linked to each other, but another component may be "interposed" between the respective components, or the respective components may be "connected", "coupled", or "linked" through another component.

Further, a singular form used in the present invention may include a plural form if there is no clearly opposite meaning in the context. In the present invention, a term such as "comprising" or "including" should not be interpreted as necessarily including all various components or various steps disclosed in the present invention, and it should be interpreted that some component or some steps among them may not be included or additional components or steps may be further included.

In addition, in this specification, when the component is called "A and/or B", the component means, A, B or A and B unless there is a particular opposite statement, and when the component is called "C or D", this means that the term is C or more and D or less unless there is a particular opposite statement.

The present invention relates to a magnetic particle imaging device having a field of view (FOV) wide enough to be applicable to the human body. Hereinafter, the magnetic particle imaging device according to an exemplary embodiment of the present invention will be described in detail with reference to FIGS. 1 to 14.

Figure 2:
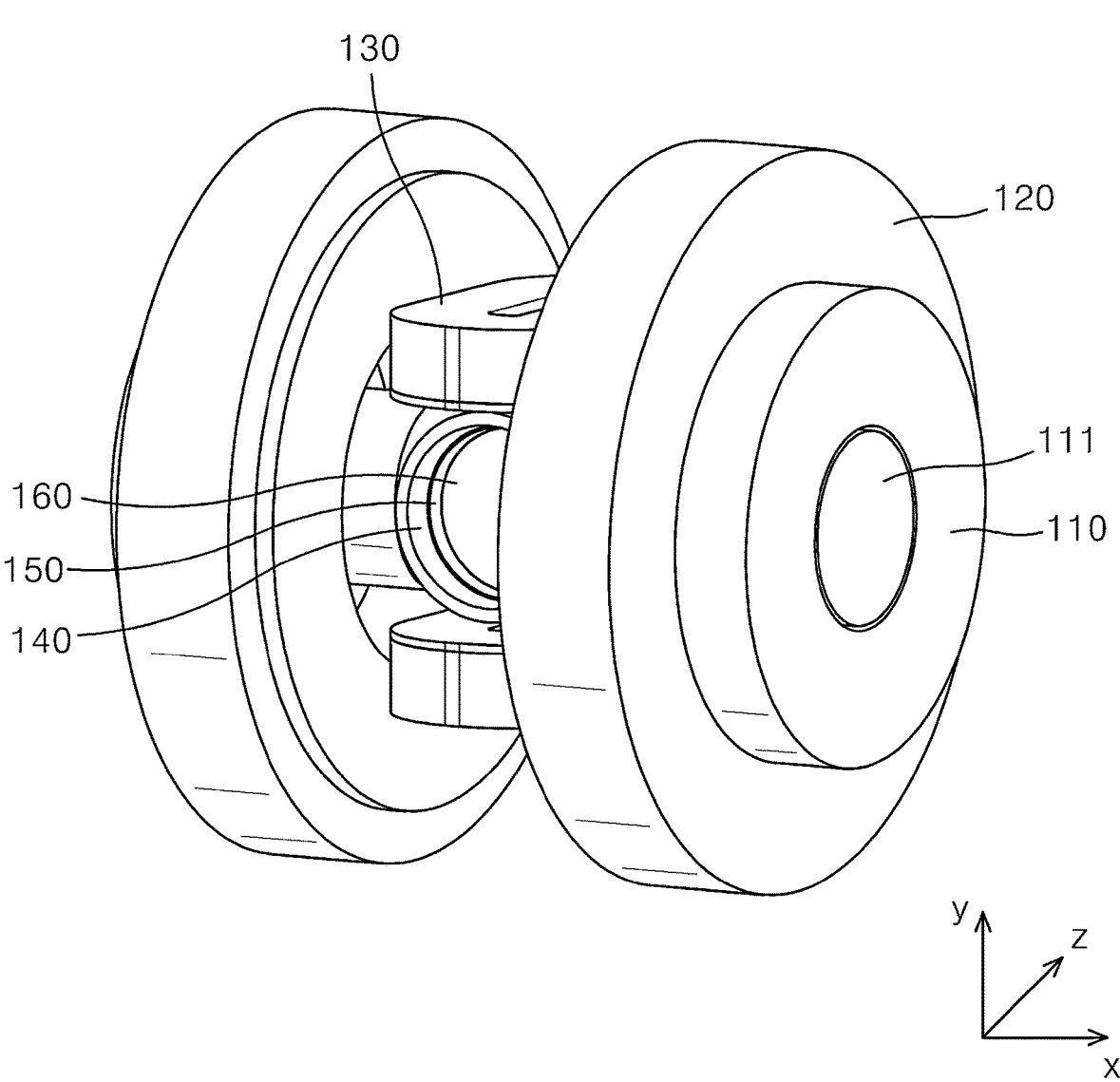
Figure 3:
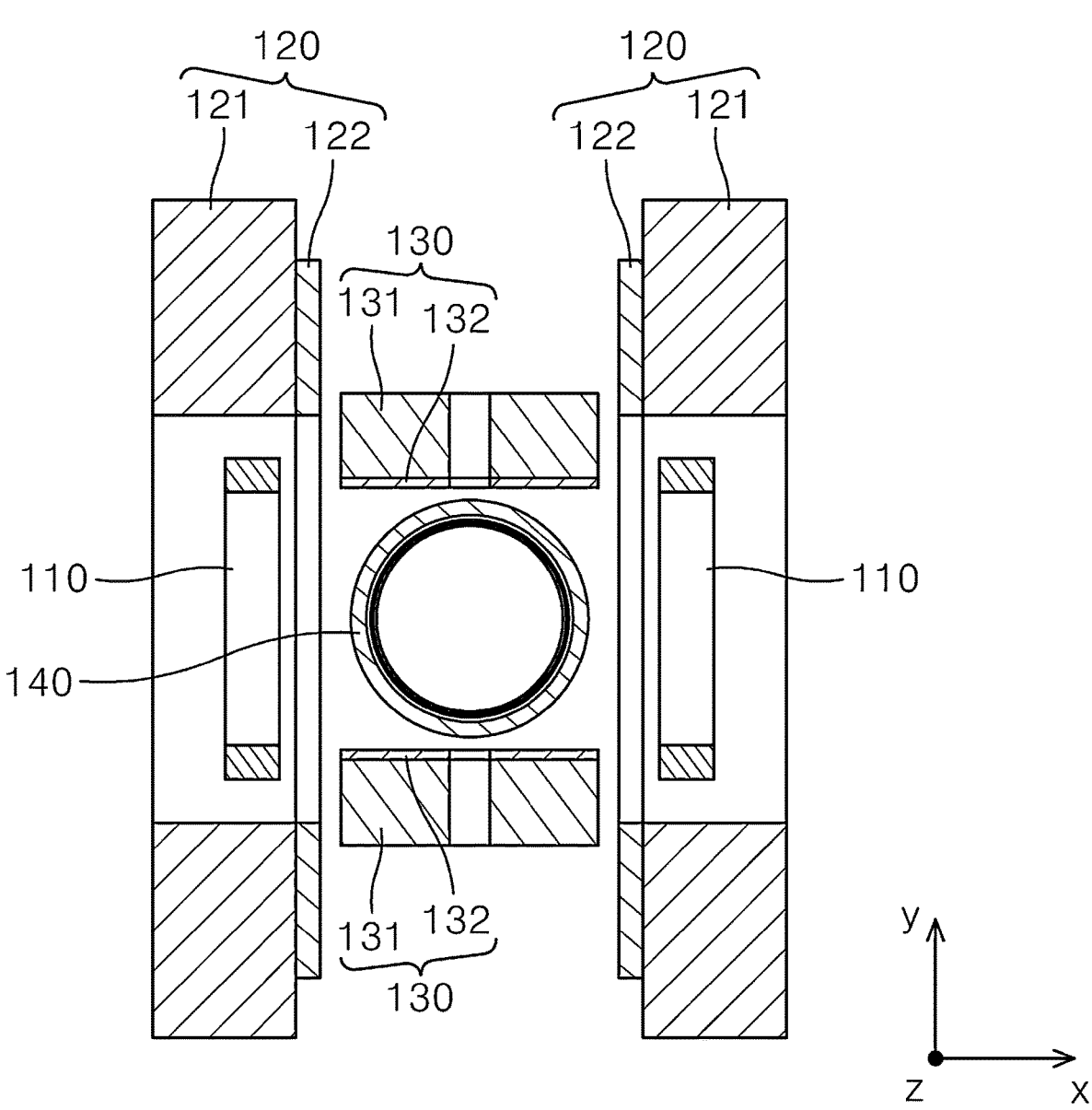
FIGS. 3 and 4 are longitudinal cross-sectional views of the magnetic particle imaging device according to each exemplary embodiment of the present invention.
Figure 4:
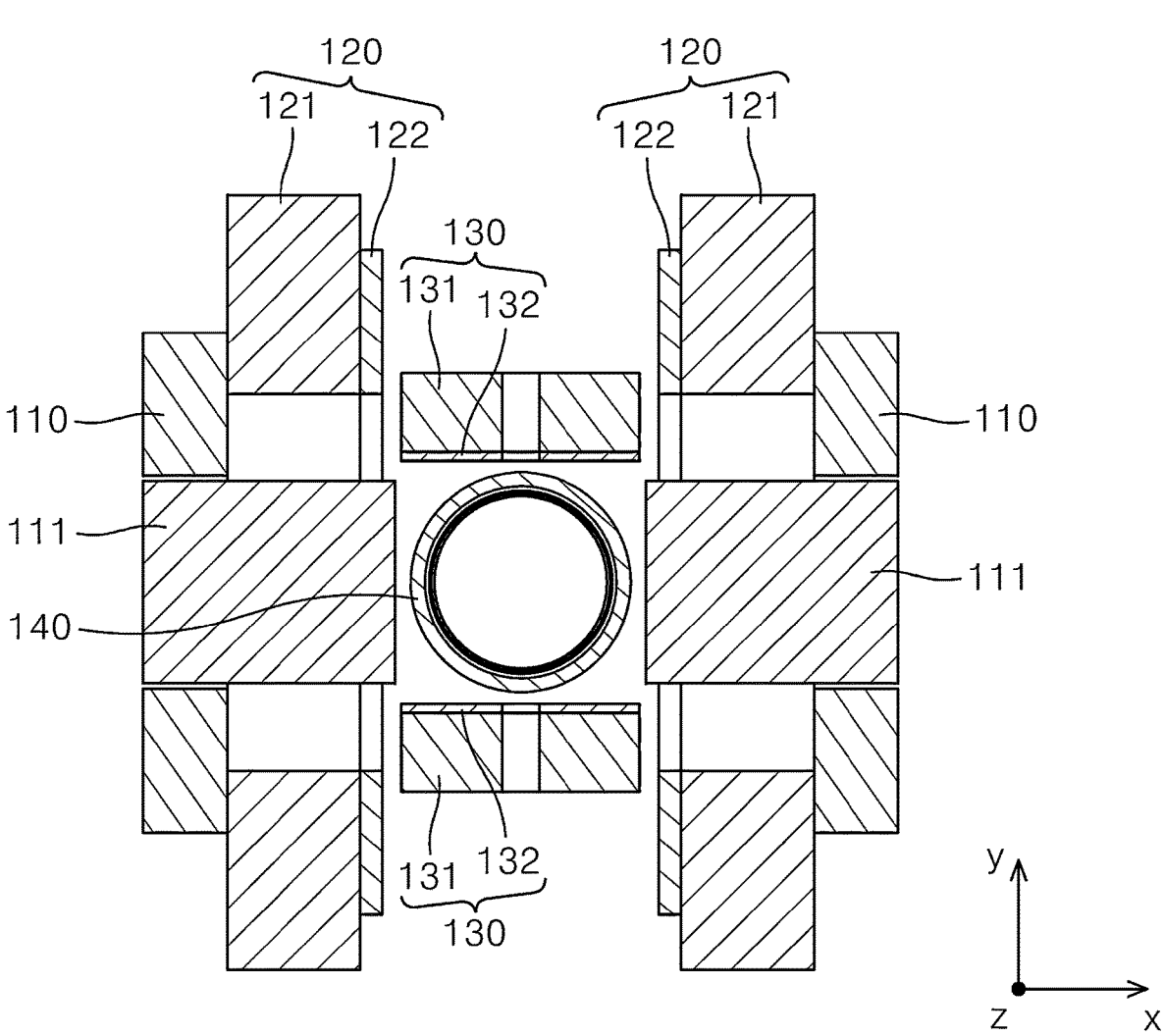
Figure 5:
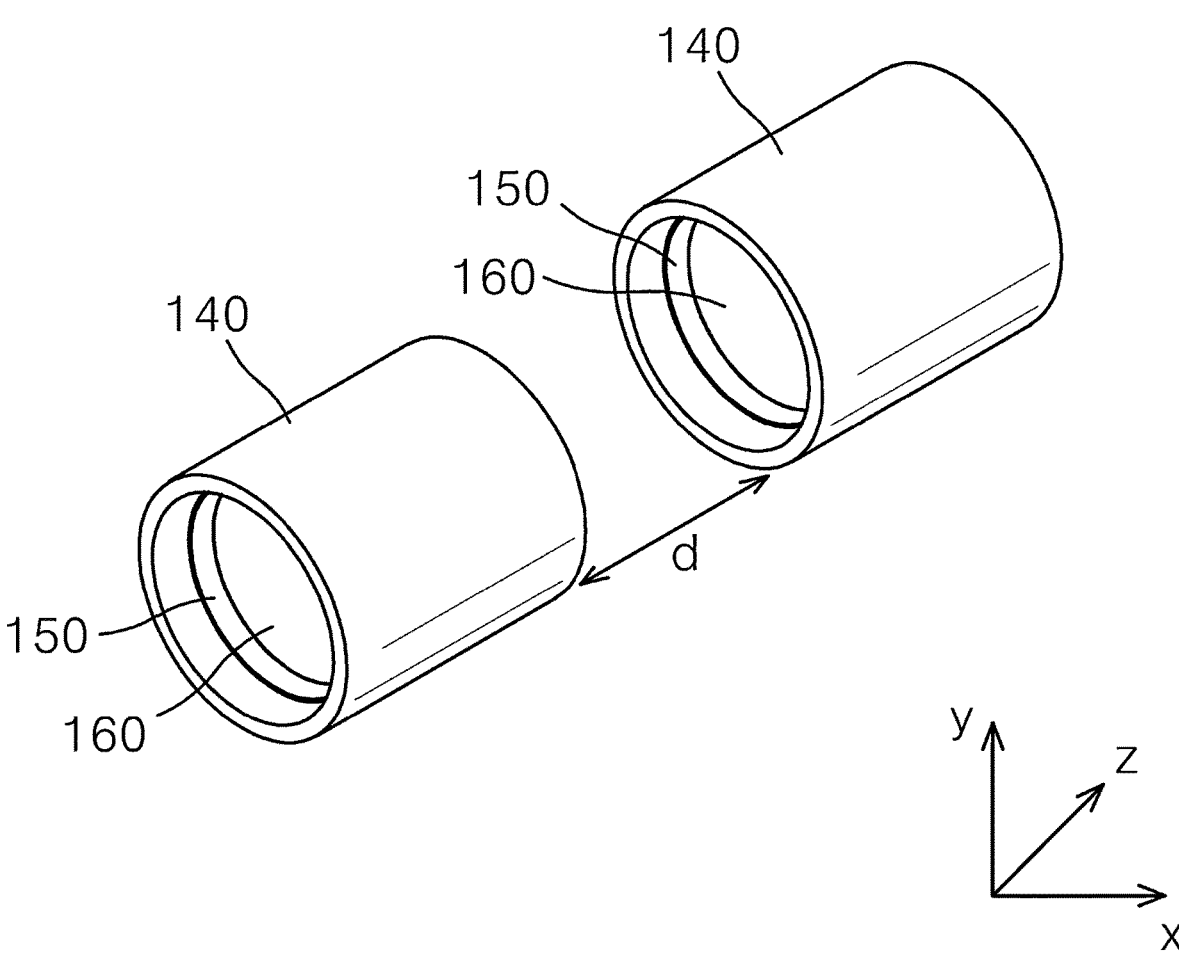
FIG. 5 is a diagram separately illustrating an operation coil unit, an excitation coil unit, and a reception coil unit corresponding to a z-axis direction.

FIGS. 1 and 2 are diagrams illustrating a magnetic particle imaging device according to each embodiment of the present invention, and FIGS. 3 and 4 are longitudinal cross-sectional views of the magnetic particle imaging device according to each exemplary embodiment of the present invention. Further, FIG. 5 is a diagram separately illustrating an operation coil unit, an excitation coil unit, and a reception coil unit corresponding to a z-axis direction.

Figure 6:
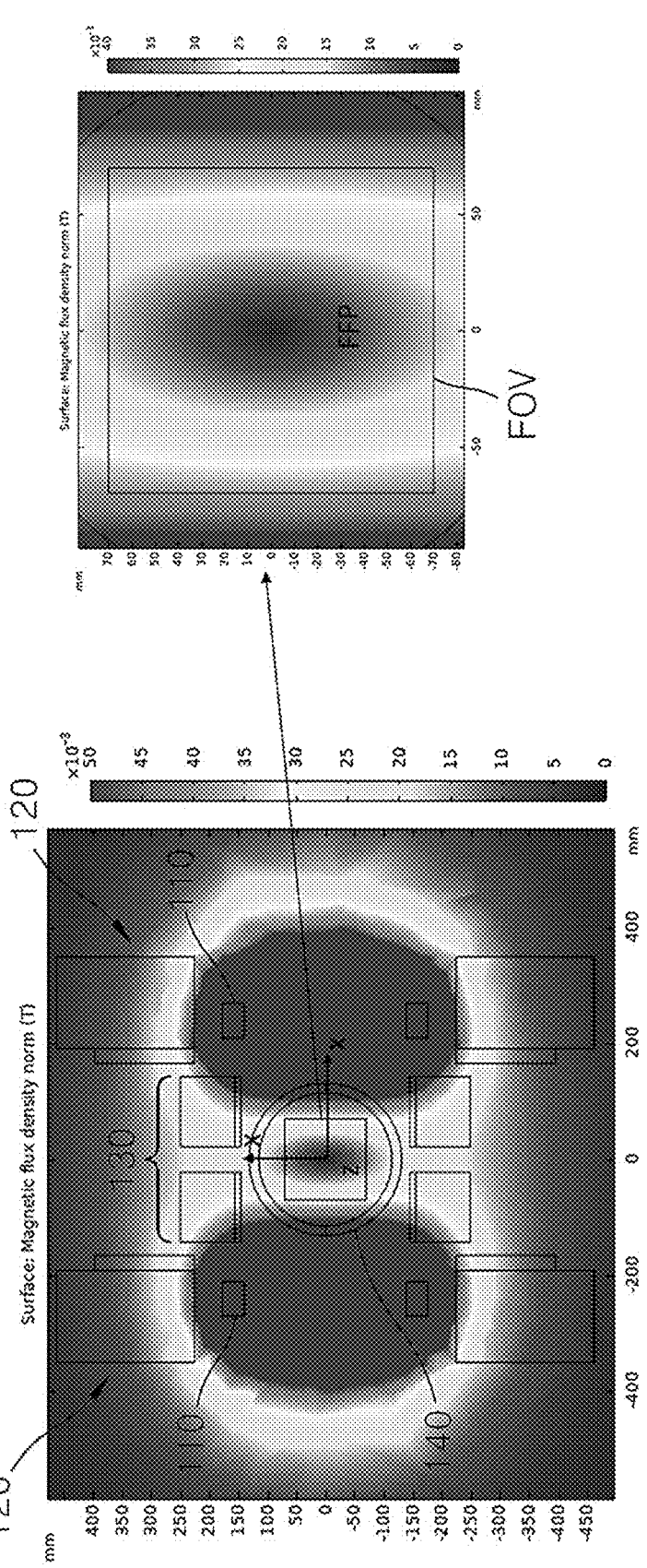
FIG. 6 is a diagram illustrating a magnetic field generated in the magnetic particle imaging device illustrated in FIG. 1 and the resulting FFP.
Figure 7:
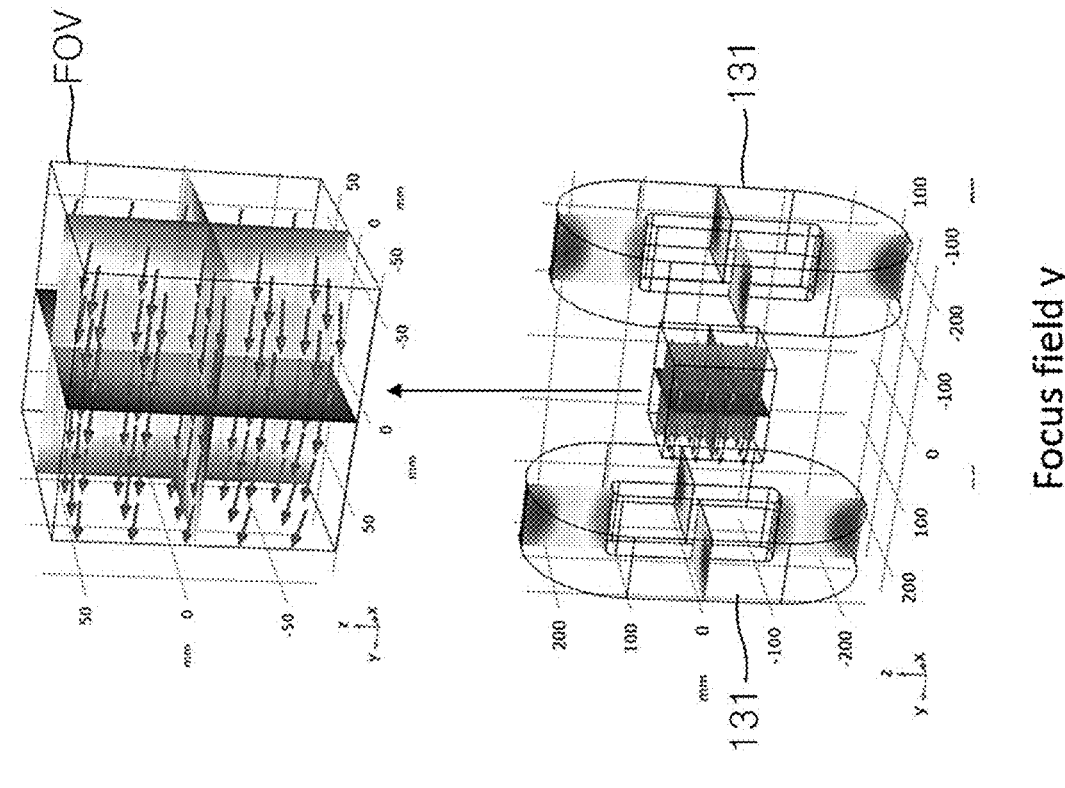
FIG. 7 is a diagram illustrating a magnetic field in an FOV generated by a focus coil.
Figure 8:
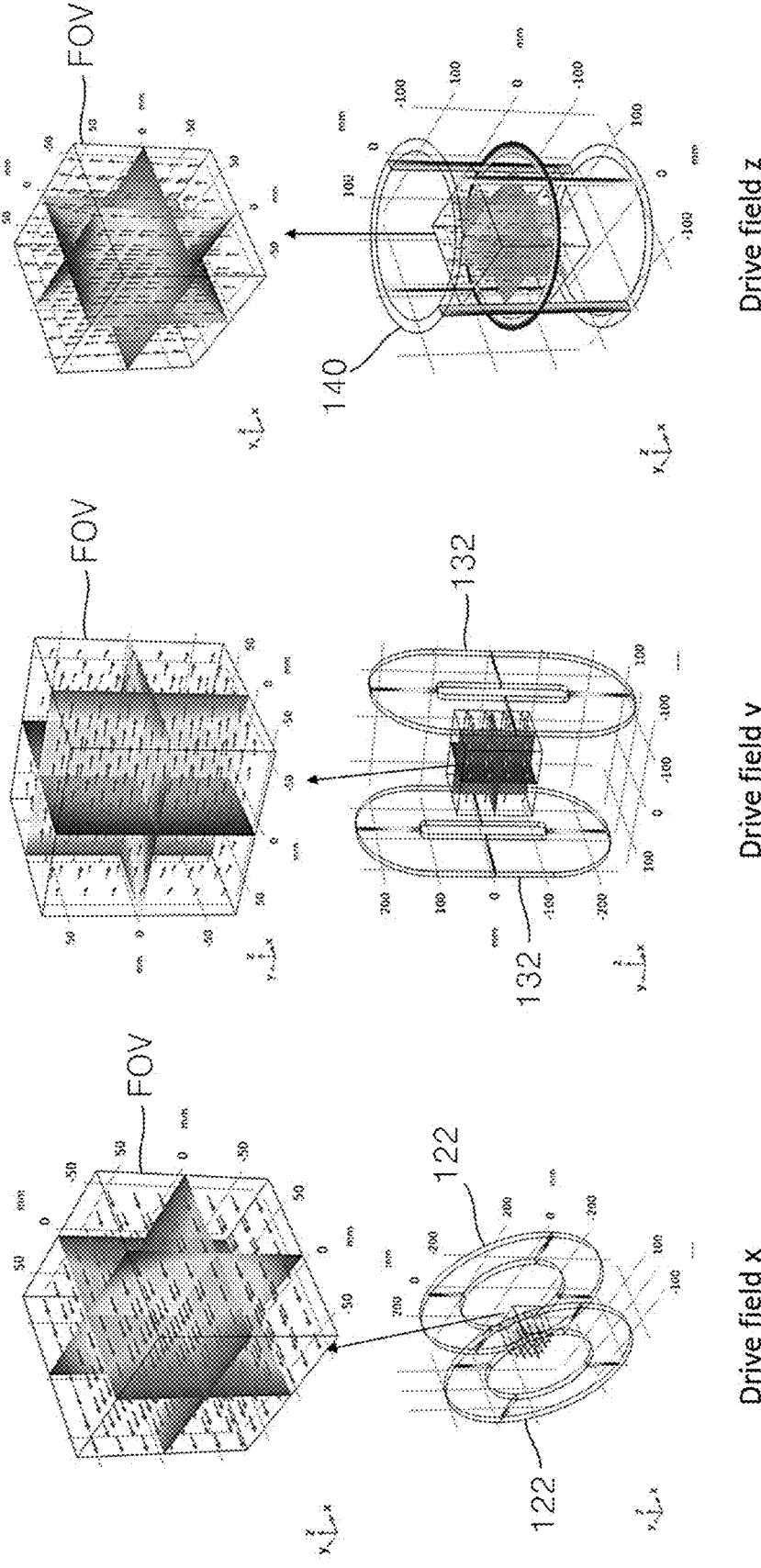
FIG. 8 is a diagram illustrating the magnetic field in the FOV generated by a drive coil.
Figure 9:
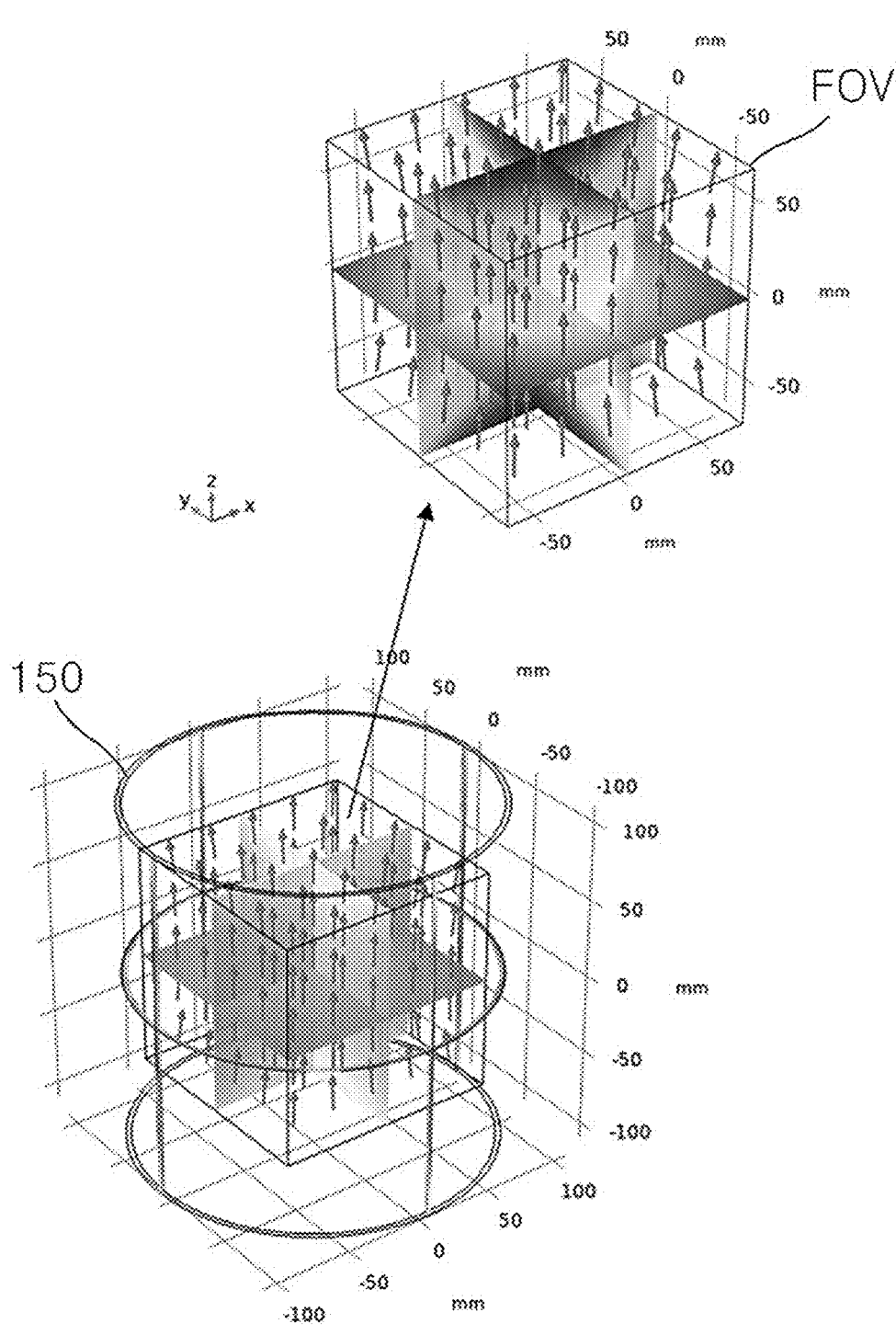
FIG. 9 is a diagram illustrating the magnetic field in the FOV generated by an excitation coil unit.

FIG. 6 is a diagram illustrating a magnetic field generated in the magnetic particle imaging device illustrated in FIG. 1 and the resulting FFP. FIG. 7 is a diagram illustrating a magnetic field in an FOV generated by a focus coil, FIG. 8 is a diagram illustrating the magnetic field in the FOV generated by a drive coil, and FIG. 9 is a diagram illustrating the magnetic field in the FOV generated by an excitation coil unit.

Figure 10:
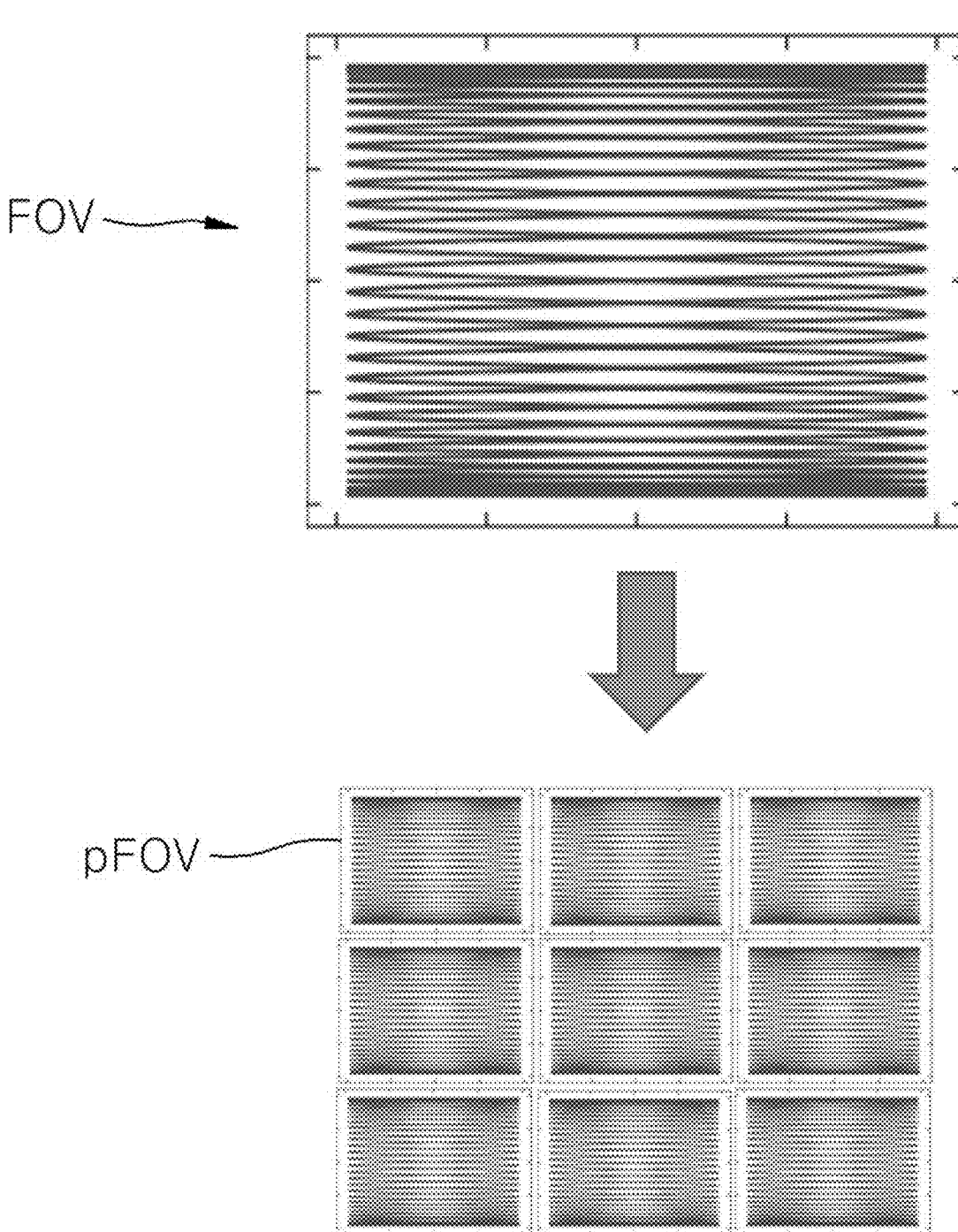
FIG. 10 is a diagram illustrating a state in which the FOV is divided into partial FOVs.
Figure 11:
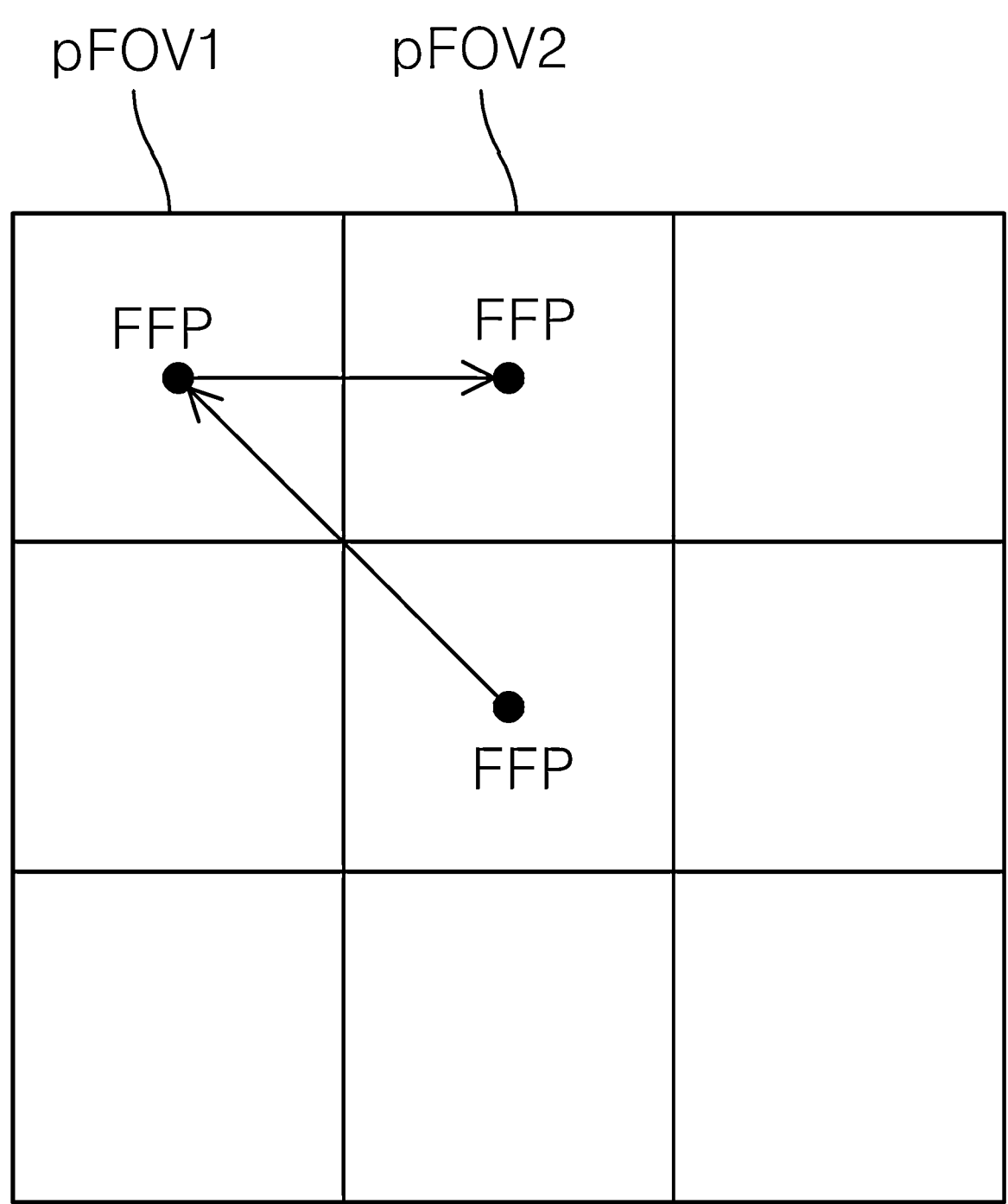
FIG. 11 is a diagram illustrating a state in which the FFP is moved into the partial FOV through control of the focus coil.
Figure 12:
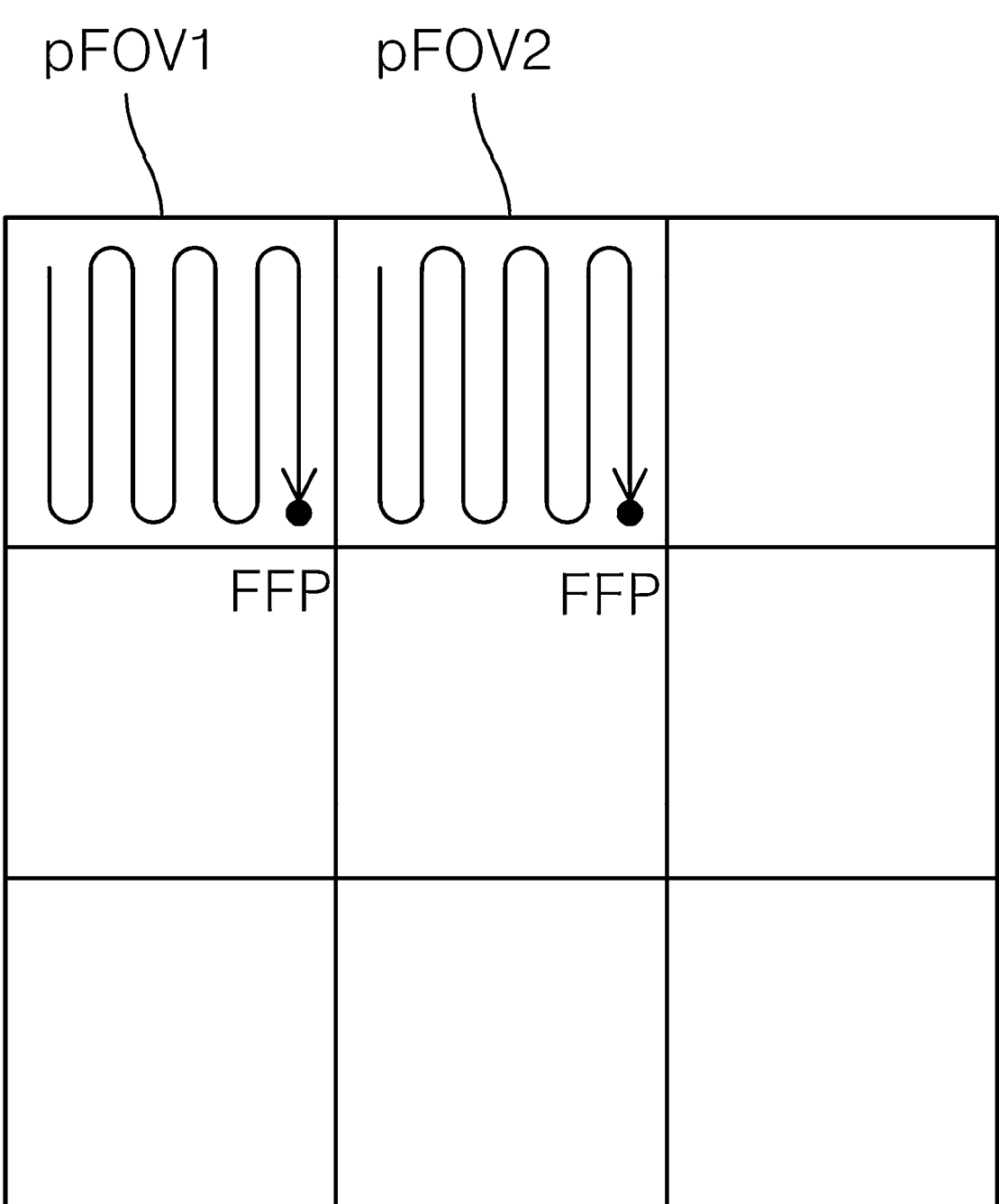
FIG. 12 is a diagram illustrating a state in which the FFP is moved within each partial FOV through control of the drive coil.

FIG. 10 is a diagram illustrating a state in which the FOV is divided into partial FOVs. FIG. 11 is a diagram illustrating a state in which the FFP is moved into the partial FOV through control of the focus coil and FIG. 12 is a diagram illustrating a state in which the FFP is moved within each partial FOV through control of the drive coil.

Figure 13:
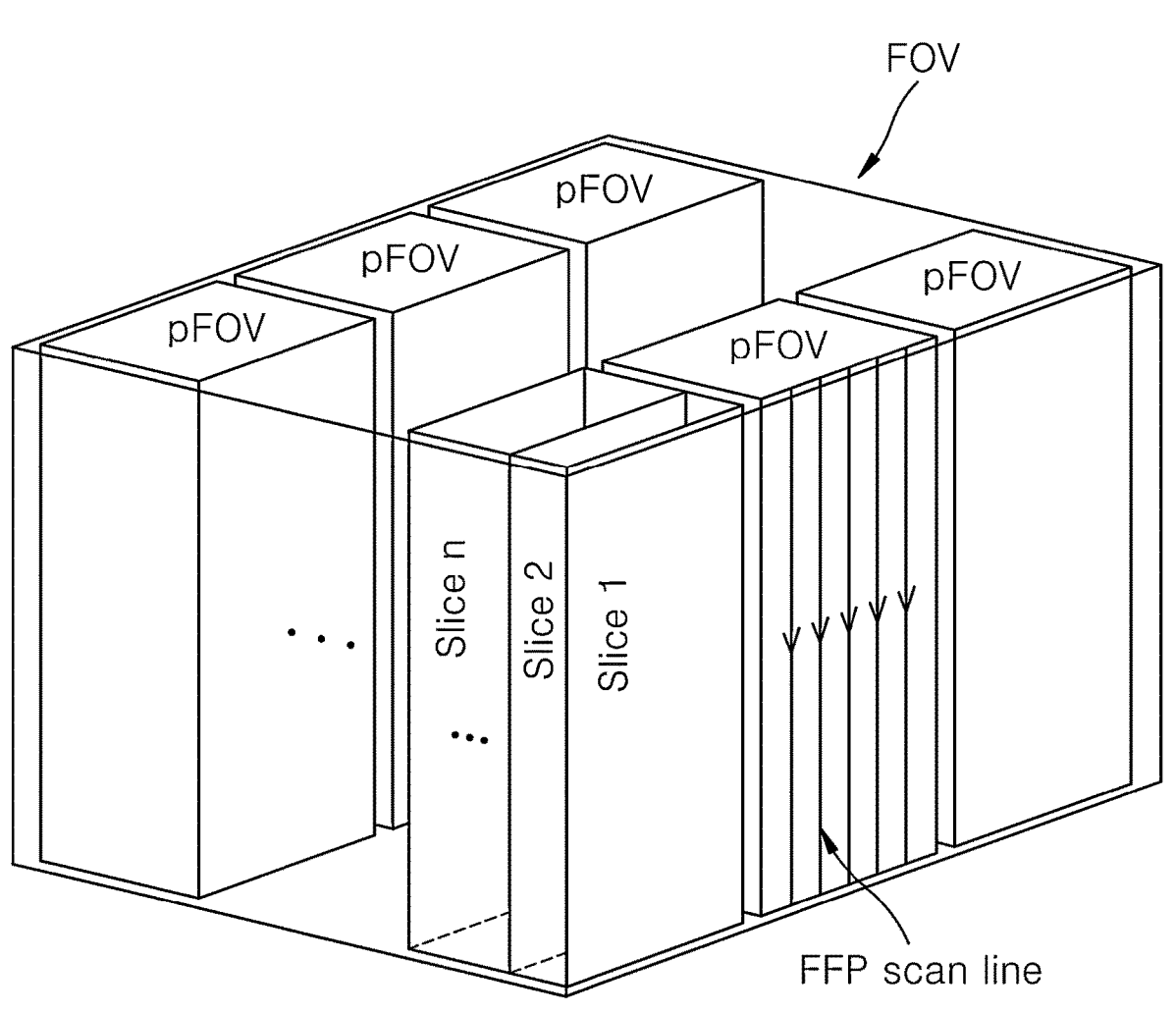
FIG. 13 is a diagram illustrating a relationship between the FOV and the partial FOV 3-dimensionally.
Figure 14:
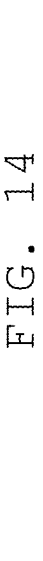
FIG. 14 is a diagram illustrating a process of generating an entire image for the FOV based on a partial image for the partial FOV.

FIG. 13 is a diagram illustrating a relationship between the FOV and the partial FOV 3-dimensionally and FIG. 14 is a diagram illustrating a process of generating an entire image for the FOV based on a partial image for the partial FOV.

Referring to FIGS. 1 to 4, the magnetic particle imaging device according to an exemplary embodiment of the present invention may include an FFP generation unit 110, first to third operation coil units 120, 130, and 140, an execution coil unit 150, a reception coil unit 160, and a processor (not illustrated). However, the magnetic particle imaging device illustrated in FIGS. 1 to 4 follows an exemplary embodiment and the components are not limited to the exemplary embodiment illustrated in FIGS. 1 to 4 and as necessary, some components may be added, modified, or deleted.

The magnetic particle imaging device of the present invention may basically detect a harmonic signal according to non-linear characteristics in which a magnetic particle has a gradient magnetic field, and acquire an image based thereon.

To this end, a field free point (hereinafter, referred to as FFP) in which a magnetic field is sparse should be generated within a field of view (hereinafter, referred to as FOV), and in the present invention, the FFP may be generated by using an FFP generation unit 110 exemplified as two structures.

Referring to both FIGS. 1 and 3, in one example, the FFP generation unit 110 may be implemented as a pair of superconductors 110 disposed to face each other in a first direction with the FOV interposed therebetween. Meanwhile, in this specification, first to third directions as directions having a vertical relationship with each other, and hereinafter, for convenience of description, the first to third directions are mixed as x-axis, y-axis, and z-axis directions, respectively.

Supercurrent in opposite directions may flow on two superconductors 110 disposed to be opposite to each other in the x-axis direction and facing each other with the FOV interposed therebetween, and two superconductors 110 may generate a strong gradient magnetic field in the FOV. The magnetic fields generated in the respective superconductors 110 may be overlapped, and as a result, the FFP may be generated in the FOV.

Referring to FIGS. 2 and 4, in another example, the FFP generation unit 110 may be implemented as a pair of selection coils 110 disposed to be opposite to each other in the first direction with the FOV interposed therebetween. In this case, two selection coils 110 may function like a Maxwell coil.

Specifically, as two selection coils 110 are disposed to be opposite to each other in the x-axis direction, opposite-direction currents may flow on two selection coils 110 facing each other with the FOV interposed therebetween, and two selection coils 110 may generate a gradient magnetic field in the FOV. The magnetic fields generated in the respective selection coils 110 may be overlapped, and as a result, the FFP may be generated in the FOV.

Meanwhile, when the FFP generation unit 110 is implemented as the selection coil 110, the intensity of the gradient magnetic field generated in the FOV may be weaker than that when the FFP generation unit 110 is implemented as the superconductor 110. When the intensity of the gradient magnetic field is weak, the resolution of the image generated by the magnetic particle imaging device may be lowered, so the present invention may amplify a magnitude of the gradient magnetic field by using a core 111.

Referring back to FIGS. 2 and 4, the magnetic particle imaging device may further include a pair of cores 111 surrounded by a pair of selection coils 110. Specifically, each selection coil 110 may be wound on a ferromagnetic core 111 in order to serve as an electromagnet, and the intensity of the magnetic field generated by the selection coil 110 may be amplified according to a magnetic permeability of the core 111.

As described above, the magnetic particle imaging device may have two types of shapes according to the structure of the FFP generation unit 110, and hereinafter, for convenience of description, it is assumed that the magnetic particle imaging device has shapes illustrated in FIGS. 1 and 3.

The magnetic particle imaging device may include first to third operation coil units 120, 130, and 140, which move the FFP in the first to third directions which are vertical to each other, respectively. Hereinafter, the structure of each of the operation coil units 120, 130, and 140 will be described. Referring back to FIGS. 1 and 3, the first operation coil unit 120 may be disposed to be opposite in parallel to the FFP generation unit 110. More specifically, centers of the FFP generation unit 110 and the first operation coil unit 120 may be the same as each other, and the FFP generation unit 110 may be disposed to be surrounded by an inner circumferential surface of the first operation coil unit 120. As a result, the first operation coil units 120 may also be disposed to be opposite in the x-axis direction with the FOV interposed therebetween similarly to the FFP generation unit 110.

The first operation coil unit 120 may include a pair of first focus coils 121 and a pair of first drive coils 122 which generate a uniform magnetic field in the x-axis direction and move the FFP in the x-axis direction. In this case, the first drive coil 122 may be disposed to be adjacent to an inner surface of the first focus coil 121.

Both the first focus coil 121 and the first drive coil 122 are used for moving the FFP in the x-axis direction, but the first focus coil 121 may have more turns in order to generate a magnetic field having a larger amplitude than the first drive coil 122. Distinguished operations of the focus coils 121 and 131 and the drive coils 122 and 132 will be described below.

Further, the second operation coil unit 130 may be disposed between the first operation coil units 120. Specifically, the second operation coil units 130 may be disposed to be opposite to each other in the y-axis direction between a pair of first drive coils 122. The second operation coil unit 130 may include a pair of second focus coils 131 and a pair of second drive coils 132 which generate the uniform magnetic field in the y-axis direction and move the FFP in the y-axis direction. In this case, the second drive coil 132 may be disposed to be adjacent to the inner surface of the second focus coil 131.

Similarly, both the second focus coil 131 and the second drive coil 132 are used for moving the FFP in the y-axis direction, but the second focus coil 131 may have more turns in order to generate the magnetic field having the larger amplitude than the second drive coil 132. Distinguished operations of the focus coils 121 and 131 and the drive coils 122 and 132 will be described below.

Referring to FIGS. 1, 3, and 5 jointly, the third operation coil unit 140 may be disposed between the second operation coil units 130. Specifically, the third operation coil units 140 may be disposed to be extended in the z-axis direction between a pair of second drive coils 132. In other words, the third operation coil unit 140 may have a cylindrical shape extended in the z-axis direction.

The third operation coil unit 140 may include a third drive coil 140 that generates the uniform magnetic field in the z-axis direction and moves the FFP in the z-axis direction. Meanwhile, even though the partial FOV is formed only in the x-axis and y-axis directions as described below, a z-axis image of each partial FOV may be generated, so the third operation coil unit 140 may not include a separate focus coil.

As illustrated in FIG. 5, a pair of third drive coils 140 may be provided, which are spaced apart from each other at a predetermined interval d. In this case, only any one drive coil 140 of a pair of third drive coils 140 may be disposed between the second operation coil units 130, and an internal space of the drive coil 140 may be the FOV.

Referring to FIG. 6, in the above-described structure, the processor first drives the FFP generation unit 110 to generate the FFP at the center of the FOV formed inside the third drive coil 140.

Referring to FIGS. 7 and 8, after generating the FFP, the processor controls the first to third operation coils 120, 130, and 140 to generate the uniform magnetic field in a specific direction in the FOV, and the FFP may move in the direction of the magnetic field. Distinguished driving schemes of the focus coils 121 and 131 and the drive coils 122 and 132 will be described below.

When the FFP is moved in the FOV by the first to third operation coil units 120 130, and 140, the excitation coil unit 150 generates an additional magnetic field in the FOV to excite the magnetic particle in the FOV.

In this case, the magnetic field generated by the excitation coil unit 150 as a harmonic magnetic field may have a higher frequency than the magnetic field generated in the drive coils 122, 132, and 140. Further, the magnitude of the magnetic field generated in the excitation coil may be controlled to be lower than the magnitude of the magnetic field generated in the drive coils 122, 132, and 140 in order for the magnetic field generated in the excitation coil unit 150 not to influence a pre-adjusted position of the FFP.

The reception coil unit 160 may receive a magnetic signal generated from the magnetic particle. Specifically, the reception coil unit 160 converts a non-linear signal generated by magnetizing the magnetic particle in a mixed magnetic field among linearly received signals into induced electromotive force to sense the corresponding signal.

Meanwhile in this specification, the magnetic particle may be a superconductive material (e.g., a superparamagnetic nano particle) generating the non-linear signal when being excited in the mixed magnetic field, and when the magnetic particle imaging device of the present invention is used for detecting a cancer cell, the magnetic particle may include a receptor combined with the cancer cell.

Referring to FIGS. 5 and 9 jointly, the excitation coil unit 150 may be disposed to be surrounded by the inner circumference surface of the third operation coil unit 140, and the magnetic field generate din the first to third operation coil units 120, 130, and 140, i.e., the magnetic field formed in the FOV is mixed with the harmonic magnetic field to excite the magnetic particle.

The reception coil unit 160 may be disposed to be surrounded by the inner circumference surface of the excitation coil unit 150, and may include a first reception coil wound in one direction and a second reception coil disposed to be spaced in a third direction and wound in the other direction which is an opposite direction to one direction.

When specifically described with reference to FIG. 5, a pair of third operation coil units 140 may be provided as described above. As a result, a pair of excitation coil units 150 surrounded by the inner circumferential surface of the third operation coil unit 140 may also be provided, and a pair of reception coil units 160 surrounded by the inner circumferential surface of the excitation coil unit 150 may also be provided.

The reception coil unit 160 may be constituted by two reception coils spaced apart from each other and having the same turns in order to selectively receive only the magnetic signal generated in the magnetic particle except for the magnetic field mixed with the FOV. Specifically, the first and second reception coils are disposed to be spaced apart from each other in the z-axis direction, and connected by one wire and provided in opposite winding directions, but with the same turns.

As a result, the magnetic fields generated in the first to third operation coil units 120, 130, and 140 and the excitation coil unit 150 may induce electromotive forces which have the same magnitude and are in opposite directions to the first and second reception coils, respectively, and since the electromotive forces are offset, the reception coil unit 160 may selectively receive only the signal generated in the magnetic particle.

The processor may generate the image for the FOV based on the received magnetic signal, and has a problem in that as the magnitude of the gradient magnetic field generated in the FFP generation unit 110 is rapidly reduced in the FOV wide enough to be applicable to the human, the resolution of the image is low. In order to solve the problem, there is an additional problem in that when a magnetic field having a large amplitude and a high frequency is used, the magnitude of the magnetic field becomes excessively larger, which causes the peripheral nerve stimulation (PNS).

Referring to FIG. 10, in order to solve the problem, the processor of the present invention may divide the FOV into a plurality of partial FOV (pFOV), and generate the image for the entire FOV by using the image for each partial FOV. Here, the partial FOV as an area virtually divided by the processor, and will be described by assuming that the FOV is divided into nine partial FOVs for convenience of description.

The processor may control the first to third operation coils 120, 130, and 140 so that the FFP moves in each partial FOV. Specifically, the processor may divide the movement of the FFP into a step (hereinafter, referred to as a movement step in which the FFP moves to the partial FOV and a step (hereinafter, referred to as a scanning step) in which the FFP moves in the partial FOV, and primarily control the first to third operation coil units 120, 130, and 140 so that the movement step is performed, and then secondarily control the first to third operation coil units 120, 130, and 140 so that the scanning step is performed.

Referring back to FIGS. 7 and 8, the first and second focus coils 121 and 131 may generate a magnetic field having a lower frequency rather than a larger amplitude than the first to third drive coils 111, 132, and 140. That is, the focus coils 121 and 131 may generate a magnetic field having a relatively larger amplitude and lower frequency, and the drive coils 122 and 132 may generate a magnetic field having a relatively smaller amplitude and higher frequency.

The processor may control the first and second focus coils 121 and 131 so that the movement step is performed, and then control the first to third drive coils 122, 132, and 140 so that the scanning step is performed.

Referring to FIG. 11, since the FFP moves only into each partial FOV in the movement step, a required movement distance may be longer, but a required positional precision may be lower. As a result, the processor may move the FFP into each partial FOV by using the first and second focus coils 121 and 131 that generate the magnetic field having the relatively larger amplitude and lower frequency.

On the contrary, referring to FIG. 12, since the FFP should precisely move in all areas in each partial FOV in the scanning step, the required movement distance may be lower, but the required positional precision may be higher. As a result, the processor may move the FFP into each partial FOV by using the first to third drive coils 122, 132, and 140 that generate the magnetic field having the relatively smaller amplitude and higher frequency.

Referring to FIG. 13, the movement of the FFP through the control may be performed 3-dimensionally. Specifically, the FFP may move into the partial FOVs divided in nine zones on an x and y plane through the control of the first and second focus coils 121 and 131, and the magnetic particle may be scanned in the partial FOV while the FFP moves in each partial FOV in x-axis, y-axis (slice), and z-axis (FFP line scanning) directions through the control of the first to third drive coils 122, 132, and 140.

The processor may generate the image for the entire FOV based on the magnetic signal for each partial FOV received according to the control.

Referring to FIG. 14, the processor may generate a partial image for each partial FOV based on the magnetic field received through the reception coil unit 160 in the scanning step (step 1) for each partial FOV (step 2), and generate the entire image for the FOV, i.e., a 3-dimensional by combining each partial image (step 3). Here, the generated 3D image may be additionally processed into a phantom image.

As described above, according to the present invention, there is an advantage in that the FOV is divided into multiple partial FOVs and image for respective partial FOVs are acquired and combined to acquire an image for an entire FOV, thereby acquiring a high-definition for the FOV, and applying the present invention to a clinical demonstration without a peripheral nerve stimulation.

Although the present invention has been described above by the drawings, but the present invention is not limited by the exemplary embodiments and drawings disclosed in the present invention, and various modifications can be made from the above description by those skilled in the art within the technical ideas of the present invention. Moreover, even though an action effect according to a configuration of the present invention is explicitly disclosed and described while describing the exemplary embodiments of the present invention described above, it is natural that an effect predictable by the corresponding configuration should also be conceded.

What is claimed is:

1. A magnetic particle imaging device comprising:
a field free point (FFP) generation unit generating a FFP in a field of view (FOV);
a first operation coil unit moving the FFP in a first direction;
a second operation coil unit moving the FFP in a second direction;
a third operation coil unit moving the FFP in a third direction, wherein the first direction, the second direction, and the third direction are perpendicular to each other;
an excitation coil unit generating a magnetic field in the FOV, and exciting a magnetic particle in the FOV, wherein the excitation coil unit includes a first excitation coil and a second excitation coil disposed to be spaced in the third direction;
a reception coil unit receiving a magnetic signal generated from the magnetic particle, wherein the reception coil unit includes a first reception coil wound in a first winding direction, disposed in the first excitation coil, and surrounded by an inner circumference surface of the first excitation coil, and a second reception coil disposed in the second excitation coil, surrounded by an inner circumference surface of the second excitation coil, and wound in a second winding direction which is an opposite direction to the first winding direction; and
a processor dividing the FOV into a plurality of partial FOVs, controlling the first to third operation coil units so that the FFP moves in each of the plurality of partial FOVs, and generating an image for the FOV based on the magnetic signal for each of the plurality of partial FOVs, wherein the first operation coil unit includes a pair of first focus coils and a pair of first drive coils that are disposed to be opposite to each other in the first direction, and generate a first magnetic field in the first direction, and move the FFP in the first direction, wherein the second operation coil unit includes a pair of second focus coils and a pair of second drive coils that are disposed to be opposite to each other in the second direction, and generate a second magnetic field in the second direction, and move the FFP in the second direction, wherein the third operation coil unit includes a pair of third drive coils, which are disposed to be extended in the third direction, and generate a third magnetic field in the third direction, and move the FFP in the third direction, wherein amplitudes of magnetic fields generated in the first and second focus coils are larger than amplitudes of magnetic fields generated in the first to third drive coils, and frequencies of the magnetic fields generated in the first and second focus coils are lower than frequencies of the magnetic fields generated in the first to third drive coils, wherein the processor is configured to perform:
a movement step that controls the first and second focus coils so that the FFP moves into a partial FOV of the plurality of partial FOVs; and then
a scanning step that controls the first to third drive coils so that the FFP moves within the partial FOV, wherein in the movement step, the FFP moves into the plurality of partial FOVs, wherein each of the plurality of FOVs have a cuboid shape, by moving on an x and y plane through the control of the first and second focus coils, and wherein in the scanning step, the magnetic particle is scanned in the partial FOV while the FFP moves in each of the plurality of partial FOVs in x-axis, y-axis, and z-axis directions through the control of the first to third drive coils.

2. The magnetic particle imaging device of claim 1, wherein the FFP generation unit includes a pair of selection coils disposed to be opposite to each other in the first direction with the FOV interposed therebetween.

3. The magnetic particle imaging device of claim 2, further comprising:
a pair of cores surrounded by the pair of selection coils.

4. The magnetic particle imaging device of claim 1, wherein the FFP generation unit includes a pair of superconductors disposed to be opposite to each other in the first direction with the FOV interposed therebetween.

5. The magnetic particle imaging device of claim 1, wherein the excitation coil unit excites the magnetic particle by mixing the magnetic field generated in the excitation coil with the magnetic fields generated in the first to third operation coil units.

6. The magnetic particle imaging device of claim 1, wherein the processor includes a processor that generates a partial image for the each of the plurality of partial FOVs based on the magnetic signal for each of the plurality of partial FOVs, and generates the image for the FOV by combining each of the partial images.

7. The magnetic particle imaging device of claim 1, wherein the processor generates a partial image for each of the plurality of partial FOVs based on the magnetic signal received through the reception coil unit in the scanning step for each of the plurality of partial FOVs, and generate the image for the FOV by combining each of the partial images, wherein the generated image is additionally processed into a phantom image.

* * * * *